United States Patent [19]

Vichard

[11] Patent Number: 5,318,567
[45] Date of Patent: Jun. 7, 1994

[54] SCREW-ON PLATE FOR TREATMENT OF FRACTURES OF THE ODONTOID APOPHYSIS

[76] Inventor: Olivier Vichard, Moncey, 25870 Geneuille, France

[21] Appl. No.: 963,942

[22] Filed: Oct. 20, 1992

Related U.S. Application Data

[63] Continuation of Ser. No. 724,828, Jul. 2, 1991, abandoned.

[51] Int. Cl.⁵ .............................. A61B 17/56
[52] U.S. Cl. ...................... 606/65; 606/71; 606/73
[58] Field of Search ............. 606/62, 63, 64, 65, 606/66, 67, 68, 72, 73

[56] References Cited

U.S. PATENT DOCUMENTS

| | | | |
|---|---|---|---|
| 2,612,159 | 9/1952 | Collison | 606/65 |
| 3,374,786 | 3/1968 | Callender | 606/65 |
| 3,996,931 | 12/1976 | Callender | 606/65 |
| 4,438,762 | 3/1984 | Kyle | 606/65 |
| 4,621,629 | 11/1986 | Koeneman | 606/65 |
| 4,628,923 | 12/1986 | Medoff | 606/65 |
| 4,776,329 | 10/1988 | Treharne | 606/65 |
| 4,791,918 | 12/1988 | Von Hasselbach | 606/65 |
| 4,973,332 | 11/1990 | Kummer | 606/65 |
| 4,988,350 | 1/1991 | Herberg | 606/65 |

*Primary Examiner*—Michael A. Brown
*Attorney, Agent, or Firm*—Collard & Roe

[57] ABSTRACT

A device for treating fractures of the odontoid apophysis of the second cervical vertebra (axis) by containing the osseous fragments. The device includes a plate shaped to be placed on the caudal fragment of the axis and serves as a support for the head of a screw. The plate additionally contains a barrel for guiding the screw which is threaded into the cranial fragment of the odontoid apophysis of the axis. The plate has a forked part extending on the caudal side of the axis and which part is attached to the anterior surface of the body of the third cervical vertebra. The invention prevents the head of the screw from penetrating into the caudal fragment of the axis and the self-tapping screw from brushing the fragile caudal fragment before forming a positive hold in the cortical cranial fragment.

5 Claims, 2 Drawing Sheets

SCREW-ON PLATE FOR TREATMENT OF FRACTURES OF THE ODONTOID APOPHYSIS

This is a continuation of copending application Ser. No. 07/724,828 filed on Jul. 2, 1991, now abandoned.

BACKGROUND OF THE INVENTION

1. Field of the Invention

The present invention relates to the treatment of fractures of the odontoid apophysis of the axis, or second cervical vertebra C2, and in particular, to means of containment after reduction of the osseous fragments to be fused.

Specifically, the invention relates to a plate of a shape intended to be fixed onto the third cervical vertebra C3, serving to support a screw threaded into the axis C2 to assure interfragmentary compression there in order to provide solidarity for the osseous fragments.

The odontoid apophysis or dens of the axis C2 is the essential mechanical organ for articulation of the atlas, or first cervical vertebra C1, which supports the occipital bone. It is particularly around this vertebra that all the movements of head rotation are produced. Because of this functional requirement and its corresponding shape, the odontoid apophysis is a zone of convergence of accidental forces which affect the cervical column and is therefore a zone particularly subject to fracture, with the fracture assuming a perfectly characteristic form. These fractures have been difficult to treat in a sufficiently reliable manner.

2. Discussion of the Prior Art

In the case of stable fractures, the osseous fragments can be immobilized by bringing the fragments together using a conventional external apparatus such as a compression brace. This brace however can only be used for stable fractures, where the separated fragments do not have the tendency of separating after reduction, or where there is neither anterior nor posterior displacement of the atlas C1.

In the case of unstable fractures, it is therefore necessary to use surgical techniques. These are relatively numerous, but all those currently known have major inherent insufficiencies or disadvantages. The techniques can be classified into three groups:

In mixed extra-articular arthrodesis by the posterior cervical route, the atlas C1 and the axis C2 are brought together with a metal band or a non-resorbable suture by their posterior cervical arcs. A graft is added in situ, in order to assure joining by the biological fusion of the two vertebral posterior arcs in case of rupture of the osteosynthesis suture. Under these conditions, if consolidation of the fractured odontoid apophysis does not occur, a graft is placed on the posterior arcs of C1 and C2. This combination of a band and a graft is very reliable, but the bonding of the arcs noticeably constrains head rotation. In addition, it is not practicable to allow this disabling technique to exist. While a simple band without a graft eliminates this defect, it remains too hazardous to maintain due to the possibility that the band suture may rupture.

In direct osteosynthesis by the transbuccal route, the surgeon, passing through the buccal cavity, makes an incision in the pharynx behind the base of the tongue. He then intervenes directly on the fractured odontoid apophysis onto which a consolidation plate is screwed. This technique is relatively simple and logical, but passing through the oropharynx can create serious septic complications.

In osteosynthesis by the anterior presterno-mastoid route, the odontoid apophysis is accessed first by the cervical route at the level of the anterior face of the neck, passing in front of the sterno-cleido-mastoid muscle. This technique, recommended by J. BOEHLER, carries out interfragmentary compression of the dens (odontoid apophysis) with screws, and is performed under radioscopic display with a brightness amplification. One or more screws are used, which can perforate the cranial extremity (located at the side of the cranium) of the dens. This method of operation is frequently used by doctors because it does not have the disadvantages of the other two methods discussed above. It is, however, encumbered with mechanical imperfections in its current state of development, which hinder its usefulness.

SUMMARY OF THE INVENTION

It is, therefore, an object of the present invention to provide a device for treating fractures of the occipital apophysis of the axis that does not carry the risk of complications or disability for the patient.

This object is achieved by a screw-on plate which is attached to the third cervical vertebra, and supports a screw which penetrates the cranial fragment of the dens to contain this fragment but does not adversely affect the fragile caudal fragment of the dens.

After access to the site of the fracture of the odontoid apophysis, or dens, a starting hole is normally placed into the caudal fragment of axis C2 (on the side of the coccyx) using a drill with a diameter on the order of 2 mm, in the sagittal plane of symmetry. The hole has a diameter of approximately 4 mm and is drilled to a depth of approximately 4 to 5 mm. This will allow a self-tapping screw to pass at the lance-shaped extremity. The screw, which has a head with 4 crossed crossed sides, drills its own path in the starting hole, under the force and the control of a simple screwdriver and/or jointed screwdriver. The progress of the screw can be monitored by observation on a radioscopic brightness amplifier. It is essential to obtain a stable interfragmentary compression, i.e., the hold in the cranial fragmentary of the dens, or odontoid apophysis, must be stable and solid, and the end of the screw must clear the cranial tip of this dens.

A second condition for stability is that the screw used must not brush the fragile caudal fragment of axis C2, and that the head of the screw must not penetrate into the body of the axis C2. Penetration would suppress, or at least seriously obliterate any useful compression effect between the fragments to be brought together. In general, a washer tends to prevent this undesirable penetration, but its diameter is limited for reasons of encumbrance, and gives unsatisfactory results.

This brushing of the caudal fragment of the dens of C2 is currently more or less avoided by the relative stability of certain fractures, where displacement occurs only in the sagittal plane and towards the back. The interfragmentary compression therefore prevents any displacement in the posterior direction in principle, but this can tend to elongate the dens. The mechanical effects, which can be very major in this case, and rigidity of the assembly can only be controlled by the washer associated with the head of the screw and by a perfect securement of the screw in the cortical cranial part of the dens.

In the case of sagittal anterior or mixed instability (instability both in the posterior and in the anterior direction), the infragmentary compression does not have the desired stabilizing effect because this compression tends to shorten the height of the dens, an intrinsic consequence of any anterior displacement.

It should be noted that any instability of the fracture in the frontal plane is of less importance in its amplitude relative to the preceding instability, particularly considering the great mechanical inertia and the disposition of the lateral masses, especially the transverse apophyses, of the atlas C1 and the axis C2. However, this instability is not zero, due to the clipping effect which is provoked, even by micromovements, between the interfragmentary surfaces which are in contact with each other, thus impeding the desired consolidation. An interfragmentary compression which helps to prevent microdisplacements remains the only aid in the method of screw attachment known to the current state of the art.

The invention, essentially consists of eliminating the support washer at the head of the screw, and replacing it with a larger support surface, thus suppressing any undesirable penetration of the head of the screw and/or the washer into the fragile caudal part of the odontoid apophysis or dens of the axis C2. In a preferred embodiment, a positive guide for the screw is provided in one piece with the support surface, to prevent any brushing of the screw, whether with its threaded or unthreaded part, with the fragile part of the axis C2, thus preventing any possible radial deviation affecting the surrounding osseous tissue.

Other objects and features will become apparent from the following detailed description considered in connection with the accompanying drawings which disclose the embodiments of the present invention. It should be understood, however, that the drawings are designed for the purpose of illustration only, and not as a definition of the limits of the invention.

BRIEF DESCRIPTION OF THE DRAWINGS

In the drawings wherein similar reference characters denote similar elements throughout the several views.

DETAILED DESCRIPTION OF THE PREFERRED EMBODIMENT

Figure 7B:
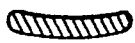
FIG. 7B is a cross-sectional view taken along plane 7B—7B of FIG. 7A.
Figure 7A:
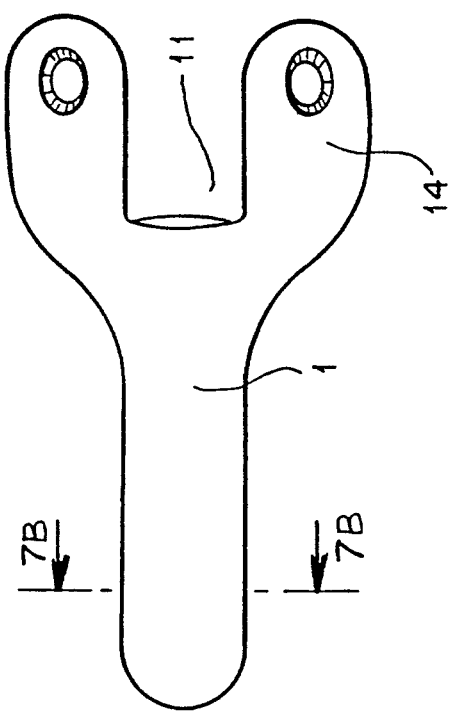
FIG. 7A is a frontal plane view, in the antero-posterior direction, of the device.

Referring to the figures, there is shown the invention in the form of a plate 1, which is slightly curved in the transverse and longitudinal (cranial-caudal) direction (as in FIG. 7B). Plate 1 rests on the anterior side of caudal fragment 2 of the axis C2 of which the odontoid apophysis or dens has fractured. Plate 1 joins caudal fragment 2 with cranial fragment 3 of the dens.

Plate 1 replaces the washer discussed earlier with respect to the known state of the art. The plate is provided with a hole 11 having an axis oriented in the caudal-cranial direction of the dens 2, 3 and has a diameter corresponding to the passage of a screw 12. The plate serves as an axial support surface for the head 13 of screw 12. This enlarged support surface better counteracts penetration of head 13 of screw 12 into the fragile caudal fragment 2 of the axis C2. Screw 12 traverses the caudal fragment 2 to achieve a positive hold in the cortical tissue of the cranial fragment 3 of C2, preferably clearing the tip of fragment 3. Screw 12 comprises a smooth cylindrical shank section between its terminal threaded section and its head, with a diameter less than that of the thread, in order not to interfere with the quality of the hold in the cranial fragment 3.

Figure 2:
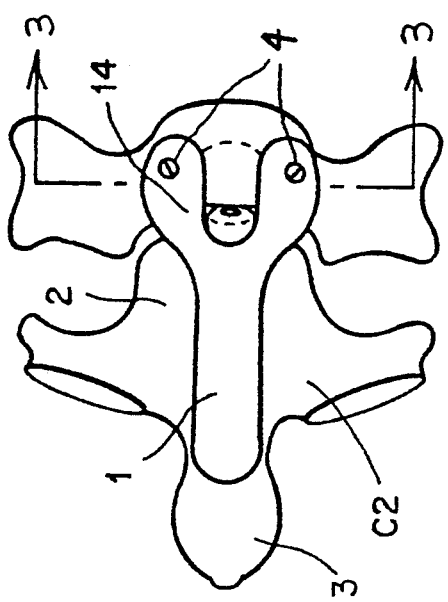
FIG. 2 is a view along a frontal plane in the anteroposterior direction of the same vertebrae C2, C3, to which a device according to the invention has been applied.
Figure 4:
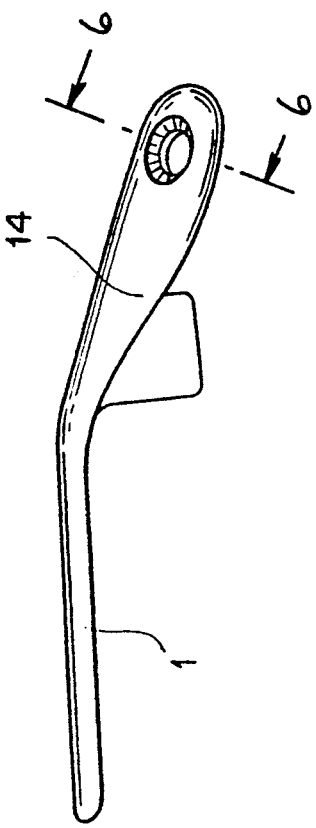
FIG. 4 is an elevational view, oriented as in FIG. 1, of the device according to the invention.
Figure 1:
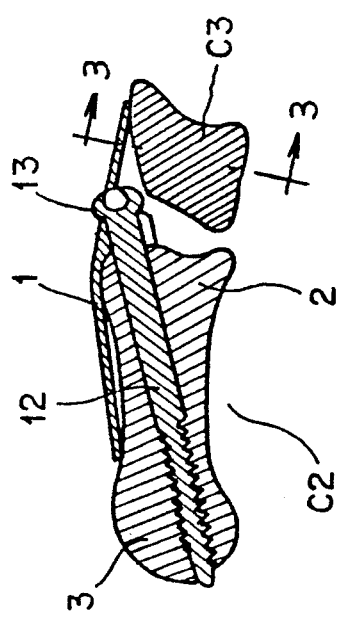
FIG. 1 is a cross-sectional view, in the sagittal plane, along the horizontal of the axis C2 and of the third cervical vertebra C3, showing the use of the device according to the invention, the cranial side being shown on the left, and the caudal side (coccyx side of the spinal column) being towards the right, with the anterior side being at the top, and the posterior side being at the bottom.
Figure 3:
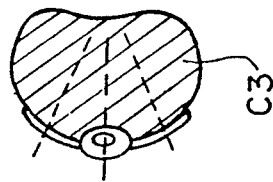
FIG. 3 is a transverse cross-sectional view, approximately horizontal, taken along plane 3—3 of FIGS. 1 and 2, of the third cervical vertebra C3.
Figure 6:
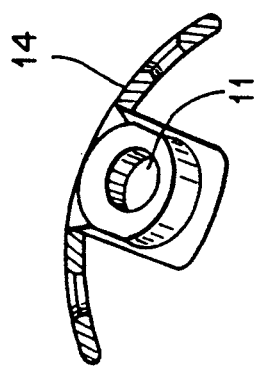
FIG. 6 is a cross-sectional view of the device of FIG. 4, taken along plane 6—6 of FIG. 4.
Figure 5:
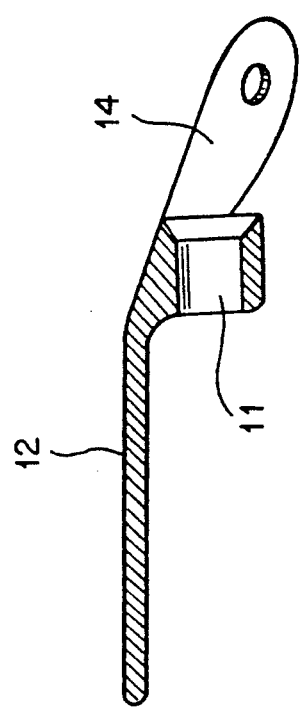
FIG. 5 is a cross-sectional view of the device of FIG. 4, taken along the sagittal plane of FIG. 1.

According to the invention, support plate 1 extends on the caudal side, beyond the passage of screw 12, and has a forked curved part 14 with a plane that is less inclined than that of the rest of plate 1 which is fastened on the anterior face of the third cervical vertebra C3 (FIGS. 1-3). This increases the mechanical stability of the hold of plate 1. Plate 1 can be fastened with a screw 4 on the third vertebra C3, as shown in FIG. 2. While the stability of head 13 of screw 12 is thus better assured in the axial direction, particularly against undesirable penetration of head 13 into the fragile caudal fragment 2 of C2, the stability of screw 12 continues to pose problems, particularly by brushing the fragile body of the caudal fragment 2 of C2. According to the invention, this disadvantage is overcome by providing support plate 1 not only with a simple passage hole, but with a guide barrel 11 for receiving screw 12. Guide barrel 11 has sufficient length, at least equal to the diameter of screw 12, to prevent any deviation of the axis or toggling of the screw 12 in any radial plane whatsoever. Screw 12 thus has a smooth shank portion with a diameter equal to that of barrel 11, and a threaded diameter equal to that of the smooth part. In the prior art, the smooth part had a diameter less than that of the threaded part, causing the incidents of brushing previously discussed. In this invention, however, the head of the screw rests on plate 1, and not on a washer with a very limited surface.

Since plate 1 is designed to be non-deformable under operating conditions, the angle between the mean planes of its parts which rest on the caudal fragment 2 of C2 and the third cervical vertebra C3 is permanently fixed, any risk of screw 12 brushing in any radial direction whatsoever is thus eliminated.

It is evident that while the invention eliminates the disadvantages of the known state of the operating technique for unstable fractures of the odontoid apophysis, it can also be advantageously applied to non-displaced and stable fractures for injured persons who find it difficult to use an external consolidation device. This is particularly the case for persons with multiple injuries, older persons, or other injured persons in a poor state of general health.

Thus, while only a single embodiment of the invention is shown and described, it is obvious that there are many changes and modifications that may be made thereunto without departing from the spirit and scope of the invention.

What is claimed is:

1. A device for the compression and interfragmentary consolidation of a fracture of the odontoid apophysis (dens) of the axis (C2) that fuses the caudal fragment with the cranial fragment, comprising:
   a plate shaped to be placed on the anterior face of the caudal fragment of the fractured dens, such plate having a barrel for receiving a screw with a head, said barrel serving as axial support for the head, said plate having a forked shape with two curved branches and a free space therebetween to permit free access to said barrel for passage of the screw, said branches being attached to the anterior surface of the body of the third cervical vertebra (C3);
   a screw passing through the space between said branches and into said barrel and secured to the cranial fragment of the dens of the second cervical vertebra (C2); and
   wherein a first mean plane of the curved part of the plate intended to rest on the third cervical vertebra (C3) is inclined relative to a second mean plane of the part of said plate resting on the caudal fragment of the dens, the angle between the mean planes corresponding to the relatively normal and stable positions of the axis (C2) and the third cervical vertebra (C3).

2. The device according to claim 1, wherein said barrel has an axis corresponding approximately to the direction of the mean axis of the dens and with a diameter corresponding to the outside diameter of the screw to assure both axial and radial stability of the screw as the screw passes into the caudal fragment and cranial fragment of the dens.

3. The device according to claim 1, wherein said two curved branches rest on and are attached to the anterior surface of the body of the third cervical vertebra (C3).

4. The device according to claim 3, comprising an additional screw, and wherein the curved part of the plate intended to rest on the third cervical vertebra (C3) is attached to the third cervical vertebra by said additional screw.

5. The device according to claim 3, wherein said plate additionally includes:
   i) A cranial portion applied to the anterior surface of the two fragments of the dens having an angle with respect to the posterior sinus; and
   ii) a caudal portion applied to the anterior surface of the body of the third cervical vertebra (C3), each of said two curved branches has a hole for a screw, said two curved branches are located on opposite sides of the sagittal plane of the human body.

* * * * *